United States Patent [19]

Huc et al.

[11] Patent Number: 4,591,456
[45] Date of Patent: May 27, 1986

[54] PROCESS FOR OBTAINING HOMOGENEOUS LAYERS OF NATIVE COLLAGEN, ITS APPLICATION IN COVERING OR ENCAPSULATING VARIOUS SUPPORTS AND THE SUPPORTS THUS COVERED

[75] Inventors: Alain Huc, Ste Foy-les-Lyon; Rene Gimeno, Pelussin; Daniel Herbage, Lyons, all of France

[73] Assignee: Bioetica, S.A., Lyons, France

[21] Appl. No.: 738,910

[22] Filed: May 29, 1985

Related U.S. Application Data

[63] Continuation of Ser. No. 596,420, Apr. 3, 1984, abandoned.

[51] Int. Cl.$^4$ .......... C08H 1/06; C08H 1/00; C08L 89/06; C09H 7/00
[52] U.S. Cl. .................... 530/356; 106/155; 106/161; 435/177; 435/188
[58] Field of Search ............ 260/123.7; 106/155, 106/161

[56] References Cited

U.S. PATENT DOCUMENTS

| 2,928,822 | 3/1960 | Johnsen et al. | 260/123.7 X |
|---|---|---|---|
| 3,152,203 | 10/1964 | Dumitru | 260/123.7 UX |
| 3,157,524 | 11/1964 | Artandi | 260/123.7 X |
| 3,393,080 | 7/1968 | Erdi et al. | 260/123.7 X |
| 3,649,347 | 3/1972 | Battista | 260/123.7 X |
| 3,823,212 | 7/1974 | Chvapil | 260/123.7 X |
| 4,185,011 | 1/1980 | Eckmayer et al. | 260/123.7 |
| 4,295,894 | 10/1981 | Cioca et al. | 106/155 |
| 4,420,339 | 12/1983 | Kato | 260/123.7 X |
| 4,451,397 | 5/1984 | Huc et al. | 260/123.7 |

FOREIGN PATENT DOCUMENTS 2524471 10/1983 France .

OTHER PUBLICATIONS

Biochim. Biophysica Acta, 194 (1969), 325–328, Herbage et al.

Primary Examiner—Howard E. Schain
Attorney, Agent, or Firm—Karl F. Ross; Herbert Dubno

[57] ABSTRACT

A new process is disclosed for obtaining homogeneous layers of native collagen. Also disclosed is a new process for covering a support with a homogeneous layer of native collagen as well as supports covered thereby.

4 Claims, No Drawings

PROCESS FOR OBTAINING HOMOGENEOUS LAYERS OF NATIVE COLLAGEN, ITS APPLICATION IN COVERING OR ENCAPSULATING VARIOUS SUPPORTS AND THE SUPPORTS THUS COVERED

This is a continuation of prior application Ser. No. 596,420, filed on Apr. 3, 1984, now abandoned.

FIELD OF THE INVENTION

This invention relates to a new process for obtaining homogeneous layers of native collagen, its application to covering or encapsulating various supports, and the supports thus covered or encapsulated by the collagen layers.

BACKGROUND OF THE INVENTION

Erhmann and Grey (J. Nat. Chem. Inst., Vol. 16, 1375–1403) were the first in 1956 to compare the growth of numerous cells and of tissue explants on collagen with cells grown on glass. They observed that in a number of cases, the collagen cells favorably influenced cellular growth.

Then in a more general manner, it was established that the collagen substrates augment growth as well as the differentiation of numerous cells in comparison with other substrates such as glass or plastic. A certain number of cells can be kept alive for a long period of time on a collagen support, and it appears that if the cells are deposited on specific collagens, additional growth factors are not necessary. The adhesion of cells to their substrate, particularly in a collagen matrix, is accomplished thanks to the specific glycoproteins of which the best described is the fibronectine group. It has been shown that certain cells utilizing the glycoproteins are able to adhere to specific collagens. For example, the fibroblasts adhere well to all types of collagens; the chondrocytes attach themselves preferably to Type II collagen and the epithelial and endothelial cells adhere best to Type IV collagen. This unique property leads to the conception of producing coverings of this protein for cellular cultures in vitro.

In addition collagen shows another characteristic which is its low antigenicity; this property is kept to a minimum by cleaving the telopeptides by chemical or enzymatic treatment. That is why this protein in its native state or freed from its telopeptides, will be able to protect synthetic materials, destined to remain in the organism. The antigenic properties of these materials will thus be masked and besides the collargen assists in the establishment of the implant by the cells which will then be able to synthesize new tissue.

Finally the collagen can be an enzyme support. Coulet and Cole, (French Pat. No. 2,235,133) have put into focus a method which permits fixing by covalent bonding of a number of enzymes to collagen, in order to conserve their activities. The efficacy of these fixed enzymes will be a fuction of the surface area of their support with respect to their reactive volumes. When the surface are with respect to the volume will be great, the enzymes will have the greatest efficacy. Thus it is necessary to use as the enzymatic reactors, either the film over which is flowed a very thin layer of the medium or very fine balls placed in a column.

The problem with the fabrication of a collagen film has been solved today (French Pat. Nos. 1,596,789 and 1,595,790) but no one as yet carried out a way to prepare balls or other non-planar supports covered with collagen.

The preparation of these objects or supports covered by collagen is especially of interest in the fields of laboratory work, medicine and industrial chemistry. Until now the preparation was either difficult or onerous or even impossible to make in view of the fact that the collagen solutions utilized for the covering processes are aqueous solutions. The drying of the objects covered with the collagen solution cannot be carried out at a temperature above that of the denaturation of collagen in solution which lies between 30°–40° C. The denaturation results in a considerable diminution of the mechanical properties of the protein, and prevents it from adhering to the object to be covered. At a temperature of less than 30° C. evaporation of the water is very slow as a consequence of the saturing vapor pressure and its affinity for the collagen. This low evaporation velocity renders impossible the obtaining of homogeneous collagen surfaces on a number of objects or supports.

In particular with non-planar objects, the solution flows away and carries the protein to the parts of the support nearest the bottom where an accumulation of material appears.

OBJECT OF THE INVENTION

The object of the present invention is to overcome these inconveniences by setting forth a process which permits obtaining homogeneous layers of native collagen, especially to cover any object or support, whatever be its form, in a very rapid manner, and more economically than in the known processes which up until now have been limited to the covering of planar objects.

SUMMARY OF THE INVENTION

In a study published in 1969 (Biochem., Biophy., Acta 194 1969, pp 325–328), Herbage et al. have shown that it is possible to dissolve purified acid-soluble collagen in an organic solvent. This research has permitted putting into focus a process for the preparation of alcoholic solutions of collagen, and it has been found possible to utilize these solutions in order to deposit a uniform layer of collagen and especially to cover or encapsulate in a uniform fashion any object or support. Thus the object of the invention is a new process to obtain homogeneous layers of native collagen and their application in the covering or encapsulation of supports of all forms.

The disclosed process involves preparing an alcoholic solution of native collagen and depositing it on the object or support to be covered by spraying or by immersion and by letting the solution run off. The aliphatic alcohol is chosen from among the monoalcohols and preferably is methanol. The vapor pressure of the methanol permits its rapid evaporation at temperatures lower than the deactiviation temperature of the collagen as well as ensures a uniform coating of the objects or supports.

The present invention will be better described and moreover its advantages will be evident by the description following which is a specific example of the preparation of an alcoholic solution of collagen and of the application of this solution to the covering of different objects or supports.

PREPARATION OF THE ALCOHOLIC SOLUTION OF COLLAGEN

The acid-soluble, purified, lyophilized collagen is prepared for example according to the technique described by Herbage et al. referred to hereinabove.

At first the chemical composition is verified to make sure that it is indeed collagen. In particular it is determined that the material contains about 333 glycine residues and about 100 hydroxy-proline residues per 1000 total amino acid residues.

The determination of the molecular mass should not show a value of less than 100,000 daltons in the aqueous solution of the protein after heating to 40° C.

Finally, an X-ray diffraction analysis examination as well as programmed differential calorimetry must confirm the entire triple helix structure characteristic of collagen.

3 grams of the collagen are dissolved in 1 liter of a solution of 0.5 M acetic acid and the solution is agitated for at least 2 hours, the centrifuging is carried out at 14,000 g for 1 hour. The supernatant is then poured into acetone in a ratio of 1 liter per 5 liters of solvent. The collagen precipitates and the precipitate is separated by centrifuging at 3000 t/m in a centrifuge of the type Robatel CF 200. The precipitate is then dissolved in a mixture of methanol and a 0.5 M aqueous acetic acid solution (50/50). After 1 hour of agitation, the total mixture is poured into an acetone bath at the rate of 1 liter of solution per 5 liters of solvent.

The precipitate is recovered as described hereinabove, then put back into solution in a mixture of methanol and a 0.5 M aqueous acetic acid solution (80/20). After 1 hour of agitation, the mixture is poured into an acetone bath in a ratio of 1 liter of solution per 5 liters of solvent. The precipitate is dissolved and put into a methanol solution at the rate of 2 g/l. After centrifuging at 30,000 g for 1 hour, the solution is put into the supply reservoir of a spray gun-pulverizer of the type Kremlin J.M. operating under a pressure of 100 g.

OBTAINING BALLS OR OTHER SUPPORTS COVERED BY COLLAGEN

Preliminary Treatment of the Support

The balls are washed for 3 successive periods of 24 hours under agitation in 3 different solutions of detergent. They are then thoroughly rinsed in deionized water and dried under vacuum at 100° C.

Covering Process, Itself 200 cc of the balls treated as described hereinabove are placed in a drageé-coater of the ERWEKA type of 10 liters, made of stainless steel, turning at a velocity of 60 t/mm. The collagen solution in the methanol is applied by spraying onto the balls moving in the drageé-coater. 3 spraying operations are carried out each for 15 seconds, separated each time by drying for 30 minutes in the drageé-coater.

The balls thus coated are subjected to a thermal treatment under vacuum at 100° C. for 24 hours, which assures reticulation of the collagen, rendered necessary by the utilization of the balls in an aqueous medium.

The quantity of the collagen deposited onto the balls can be determined according to the following: A known amount of the balls is placed in a 6N hydrochloric acid solution at 105° C. for 24 hours. Next the amount of hydroxy-proline obtained is determined according to the Stegmann method. The quantity of the deposited collagen is equal to the quantity of hydroxy-proline multiplied by 7.46.

Depositing a Collagen Film on Glass Platelets or on Petri Dishes

The glass platelets of the Petri dishes are at the very beginning carefully degreased in a mixture of chloroform-methanol. The platelets are next placed on a Teflon plate and then atomized with a solution of collagen in methanol prepared as described hereinabove. Three spraying treatments are used each for 15 seconds, separated each time by drying for 1 hour in the open air.

The Petri dishes are placed on a cloth and on each of them is deposited, with the aid of an automatic syringe, a given volume (variable according to the desired thickness) of the collagen solution in methanol. The dishes are next carried along with the cloth through a drying tunnel at 30° C. in which the air is filtered and renewed; the dishes remain in the tunnel for about 1 hour.

It is equally possible, if necessary, to subject planar supports covered as described hereinabove to the reticulation treatment described in the treatment of the non-planar supports described hereinabove.

It goes without saying that the present invention is not at all limited to the examples described hereinabove, which are non-limiting; on the contrary, the invention includes all variations which might be particularly related to the nature or form of the object or support to be coated by the layers of homogeneous, layered collagen.

We claim:

1. A process for producing a support coated with a homogeneous layer of native collagen which comprises the steps of:
    (a) forming an acid-soluble methanolic solution of native collagen;
    (b) applying the methanolic solution to a support to cover the support with a homogeneous layer of native collagen;
    (c) air-drying the coating on said support to a homogeneous layer of native collagen; and
    (d) subjecting the support coated during step (c) and after air-drying to a thermal treatment under vacuum at 100° C. for 24 hours, to assure reticulation of the collagen.

2. The process defined in claim 1 wherein in step (b), the methanolic solution is applied to the support by spraying.

3. The process defined in claim 1, wherein in step (b), the methanolic solution is applied to the support by immersing and running off.

4. A support covered by a homogeneous layer of native collagen wherein the support is covered according to the process defined in claim 1.

* * * * *